(12) United States Patent
Perry

(10) Patent No.: US 11,904,061 B2
(45) Date of Patent: Feb. 20, 2024

(54) SELF-SANITIZING STYLUS

(71) Applicant: Shannon M. Perry, Huber Heights, OH (US)

(72) Inventor: Shannon M. Perry, Huber Heights, OH (US)

(*) Notice: Subject to any disclaimer, the term of this patent is extended or adjusted under 35 U.S.C. 154(b) by 372 days.

(21) Appl. No.: 17/233,670

(22) Filed: Apr. 19, 2021

(65) Prior Publication Data

US 2021/0330833 A1 Oct. 28, 2021

Related U.S. Application Data

(60) Provisional application No. 63/014,698, filed on Apr. 23, 2020.

(51) Int. Cl.
| | | |
|---|---|---|
| *A61L 2/10* | (2006.01) | |
| *G06F 3/03* | (2006.01) | |
| *G06F 3/0354* | (2013.01) | |

(52) U.S. Cl.
CPC ............ *A61L 2/10* (2013.01); *G06F 3/03545* (2013.01); *A61L 2202/11* (2013.01); *A61L 2202/16* (2013.01)

(58) Field of Classification Search
CPC .... A61L 2/10; A61L 2202/11; A61L 2202/16; G06F 3/03545
USPC ............................ 250/453.11, 454.11, 455.11
See application file for complete search history.

(56) References Cited

U.S. PATENT DOCUMENTS

| | | | |
|---|---|---|---|
| 2015/0022503 A1* | 1/2015 | Chang .................... | B43K 23/12 345/179 |
| 2019/0143379 A1 | 5/2019 | Kitsell et al. | |
| 2019/0314536 A1 | 10/2019 | Gilliam-Perkins | |
| 2020/0237941 A1 | 7/2020 | Bonutti et al. | |

* cited by examiner

*Primary Examiner* — Nicole M Ippolito
(74) *Attorney, Agent, or Firm* — Jenei LLC; Stephen R. Jenei

(57) ABSTRACT

A self-sanitizing stylus for use in combination with a touch screen device and method of using the same is disclosed. The self-sanitizing stylus comprises a body including a component retaining enclosure and longitudinal member. The longitudinal member has a body defined between a distal end with a touch tip disposed thereon, and a proximal end secured with an operative end of the component retaining enclosure. At least one ultraviolet radiation emitting device is disposed on the body. The component retaining enclosure includes a power source and switch connected between the power source, and the ultraviolet radiation emitting device, which when pressed establishes an electrical connection between the power source and the ultraviolet radiation emitting device, which emits UV radiation to disinfect the body or portion thereof.

8 Claims, 2 Drawing Sheets

SELF-SANITIZING STYLUS

CROSS-REFERENCE TO RELATED APPLICATIONS

The present Application for Patent claims priority to U.S. Provisional Application No. 63/014,698 entitled "SELF-SANITIZING STYLUS," filed Apr. 23, 2020, which is hereby expressly incorporated by reference herein.

TECHNICAL FIELD

The present disclosure relates to a self-sanitizing or ultraviolet (UV) pen-styled stylus, which is used in combination with a touch screen device, and a method of self-sanitizing the stylus using the same.

BACKGROUND

At present we are witnessing an unprecedented surge and spread of SARS-coronavirus (referred to as COVID hereinafter) first reported in December 2019 and further characterized as a pandemic by the World Health Organization. Attempts are being made to reduce the increase and spread of the COVID by employing measures of social distancing, lockdowns, disinfecting using chemicals, and further by developing vaccines. Studies have shown that bacteria and viruses (collectively referred to as pathogens hereinafter) dwell and multiply on personal devices such as mobile phones or public keypads such as automatic teller machines (ATMs), mobile banking devices, point of sale (POS) terminals and credit card and payment devices used in retail stores. More particularly, it is observed that the pathogens found on mobile phones are similar to those found on hands. Sanitizing of the personal devices or keypads may be difficult if not impossible. One method for sanitizing of the personal devices or keypads is using chemicals. The chemicals are sprayed on the device surface to be sterilized, and then the chemical is whipped off. However, the above-mentioned method has a disadvantage that one has to carry the chemical. Further, the chemical may damage the personal device, for example, its surface or its electronic components, if the chemical infuses into the interior parts of the personal devices. Additionally, retail stores and banks have signage indicating the keypad cannot be sprayed for the above-mentioned reasons.

Additionally, some personal devices may include sleek and delicate parts such as a stylus, which is employed to enter data or provide inputs to the personal devices. The stylus itself may be contaminated with the pathogens and may not be easily decontaminated or sterilized using chemicals.

Additionally, some personal devices may include sleek and delicate parts such as a stylus, which is employed to enter data or provide inputs to the personal devices. The stylus itself may be contaminated with the pathogens and may not be easily decontaminated or sterilized using chemicals.

Further, the stylus of the personal device is more prone to contamination as the stylus or the like are handled by a human more than the personal device itself. Furthermore, the sterilization of the stylus may be also tedious due to its size and delicate structure.

Accordingly, there is felt a need to provide an alternative apparatus and a method for sterilization of the stylus and like devices, which overcomes one or more drawbacks associated with the conventional apparatuses and methods.

SUMMARY

The present disclosure provides a self-sanitizing stylus which is used in combination with a touch screen device and a method of using the same, which overcomes one or more drawbacks encountered in the prior art.

In accordance with one aspect of the present disclosure, a self-sanitizing stylus used in combination with a touch screen device is disclosed.

The self-sanitizing stylus in accordance with the present disclosure comprises a body defined by a component retaining enclosure, and a longitudinal member extending from the component retaining enclosure.

The longitudinal member has a body which is defined between a distal end with a writing tip operatively disposed thereon and a proximal end secured with an operative end of the component retaining enclosure. The body of the longitudinal member has at least one ultraviolet radiation emitting device disposed thereon.

Further, the component retaining enclosure includes a power source, and a switch, which is connected between the power source, and the at least one ultraviolet radiation emitting device, the switch adapted to selectively establish an electrical connection between the battery and the at least one ultraviolet radiation emitting device upon being switched ON, and power the at least one ultraviolet radiation emitting device, wherein the at least one ultraviolet radiation emitting device emits ultraviolet radiation, which is incident on at least a portion of the body of the longitudinal member thereby disinfecting the portion of the body.

In accordance with another aspect of the present disclosure, a method for self-sanitizing a stylus being used in combination with a touch screen device is disclosed.

The method for self-sanitizing a stylus comprising writing in combination with the touch screen device by employing the self-sanitizing stylus, pressing the switch to establish an electrical connection between the at least one ultraviolet radiation emitting device and the power source, wherein the at least one ultraviolet radiation emitting device emits ultraviolet radiation which being incident on at least a portion of the body of the longitudinal member, thereby disinfecting the portion of the body being irradiated with the ultraviolet radiation.

The at least one ultraviolet radiation emitting device is an ultraviolet light emitting diode (LED). Further, the at least one ultraviolet radiation emitting device can be a source of a UVA radiation, a UVB radiation, a UVC radiation, and a combination of UVA, UVB, and UVC radiations.

The power source can be a battery, the battery can be one of a lithium battery, and a dry cell battery. In one embodiment, the battery can be chargeable such that the self-sanitizing stylus 100 can be plugged into a power source such as a USB wall plug outlet to recharge the battery.

The switch can be one type of switch selected from the group consisting of a toggle switch, and a push button switch.

In one embodiment, the self-sanitizing stylus further comprising at least one transducer to deliver vibrational energy to the component retaining enclosure to generate and deliver a haptic feedback upon pressing the switch.

In an alternative embodiment, the self-sanitizing stylus further comprising at least one of an audio signal generator, and a visual signal generator upon pressing the switch, wherein the audio signal generator and the visual signal generator each being independently adapted to generate an audio signal and a visual signal.

In accordance with present disclosure, the self-sanitizing stylus further comprising at least one transducer to deliver vibrational energy to the component retaining enclosure to generate and deliver a haptic feedback upon pressing the switch, and a control system coupled with and for managing each of the switch, the power source, and the at least one ultraviolet radiation emitting device, the transducer, the audio signal generator, and the visual signal generator.

One of the benefits of the self-sanitizing stylus is after sanitizing or disinfecting the stylus tip, the user can safely put the device in a pocket or purse without transferring the germs to the clothes or other parts of the body.

The touch screen device is one selected from the group consisting of a mobile phone, a laptop, and a desktop. The device of the present invention can be used on public keypads such as automatic teller machines (ATMs), mobile banking devices, point of sale (POS) terminals and credit card and payment devices used in retail stores.

The touch screen device is one selected from the group consisting of a mobile phone, a laptop, and a desktop.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION OF EXAMPLE EMBODIMENTS

The present disclosure relates to a self-sanitizing stylus which is used in combination with a touch screen device, and a method of self-sanitizing the stylus using the same.

Figure 1:
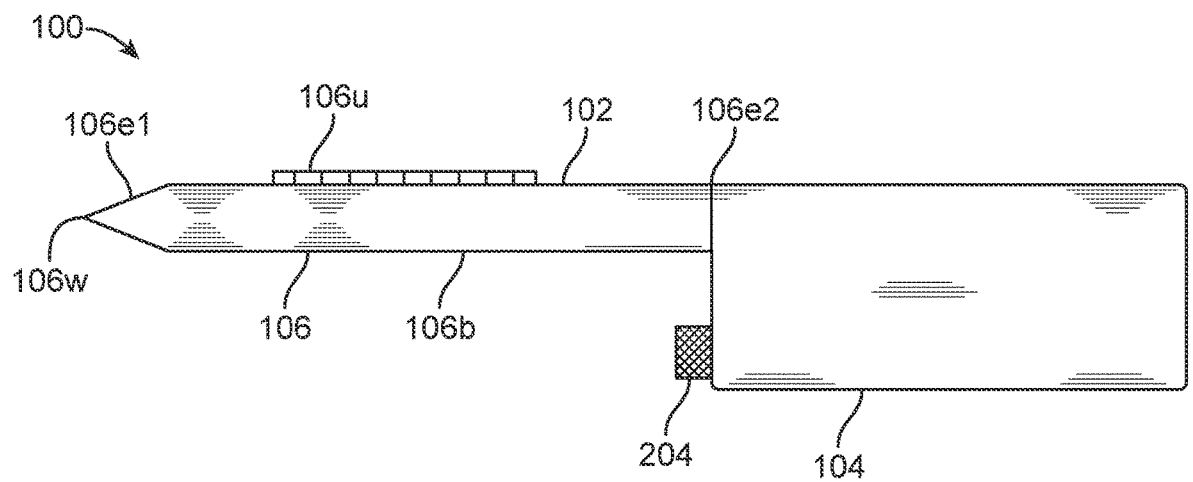
FIG. 1 illustrates a schematic diagram of a self-sanitizing stylus in accordance with the embodiments of the present disclosure.
Figure 2:
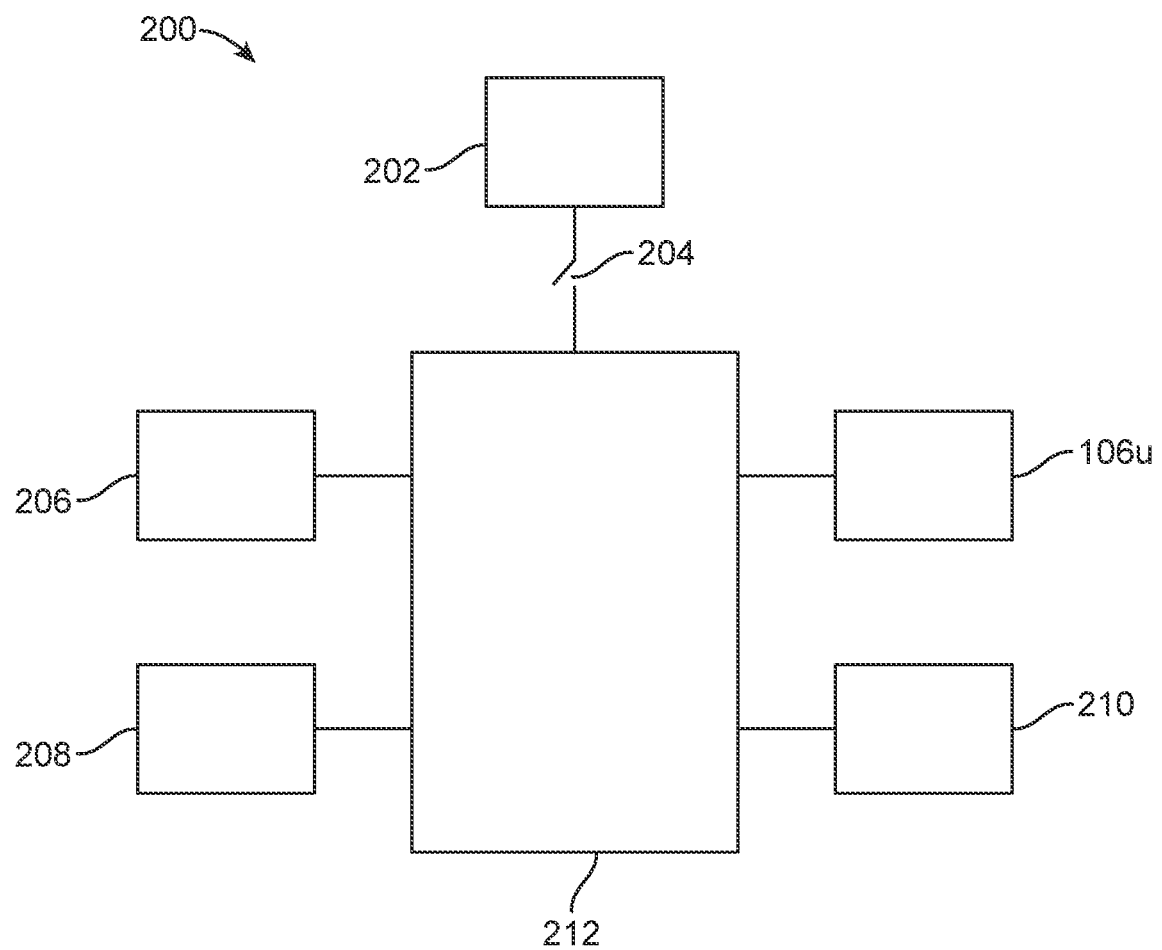
FIG. 2 illustrates a block diagram of the self-sanitizing stylus of the FIG. 1 in accordance with one embodiment of the present disclosure.

The present disclosure is described herein below with reference to the accompanying drawing wherein FIG. 1 illustrates a schematic diagram of a self-sanitizing stylus 100 in accordance with the embodiments of the present disclosure, and FIG. 2 illustrates a block diagram 200 of the self-sanitizing stylus 100 of the FIG. 1 in accordance with one embodiment of the present disclosure.

While the present invention is referred to as used with a touch-screen device, e.g., a tablet computer, electronic devices that may be used with the self-sanitizing stylus include any touch screen-enabled electronic devices including game consoles, desktop computers, laptop computers, mobile phones, smartphones, personal digital assistants (PDAs), satellite navigation devices, cameras, GPS units, interactive displays in automobiles or on appliances, and similar devices as well as with public keypads such as automatic teller machines (ATMs), mobile banking devices, point of sale (POS) terminals and credit card and payment devices used in retail stores.

A touchscreen is a component of an electronic device that functions both as a visual display output device as well as an input device that allows a user to input information into the electronic device. The touchscreen enables the user to interact directly with what is displayed, rather than using a mouse, touchpad, or any other intermediate "pointer" device (other than a stylus, which is optional for most modern touchscreens). A user may input information in the form of a simple touch or multi-touch gestures. The simple touch or multi-touch gestures may be generated by human fingers or by a suitable touch input device such as a stylus pen or other similar means that are able to generate electrical signals in the electronic device in response to the touch.

In accordance with one aspect of the present disclosure, a self-sanitizing stylus 100, which is used in combination with a touch screen device, is disclosed. The self-sanitizing stylus 100 comprises a body 102 defined by a component retaining enclosure 104, and a longitudinal member 106 extending from the component retaining enclosure 104.

The longitudinal member 106 comprises a body 106b defined between a distal end 106e1 with a touch tip 106w operatively disposed thereon, and a proximal end 106e2 secured with an operative end of the component retaining enclosure 104, and the body 106b having at least one ultraviolet radiation emitting device 106u operatively disposed thereon.

In an embodiment, the touch tip 106w material comprises a conductive rubber-based material. In another embodiment, the tip material comprises a conductive silicone-based material. In yet another embodiment, the tip material comprises a conductive polymeric fiber-based material.

The component retaining enclosure 104 comprises a power source 202, and a switch 204 connected between the power source 202 and the at least one ultraviolet radiation emitting device 106u. The switch 204 is adapted to selectively establish an electrical connection between the power source 202 and the at least one ultraviolet radiation emitting device 106u upon being switched ON. The at least one ultraviolet radiation emitting device 106u emits ultraviolet radiation on being powered by the power source 202, wherein the ultraviolet radiations are incident on at least a portion of the body 106b of the longitudinal member 106, thereby disinfecting the portion of the body 106b.

The at least one ultraviolet radiation emitting device 106u, in accordance with one embodiment of the present disclosure, can be an ultraviolet light emitting diode (LED). Any other ultraviolet radiation emitting device 106u can also be used. For example, an ultraviolet laser can also be used. Another example, of the ultraviolet radiation emitting device 106u is an ultraviolet lamp, having dimensions which can be suitably fitted onto the body 106b and can be powered using a suitable power source and electrical circuit. Thus, the present disclosure is not limited by the presently disclosed examples of ultraviolet radiation emitting devices 106u.

In one embodiment, a light-emitting diode (LED) or other similar visible light source is also provided. The LED can be activated by depression of a light button, which powers the LED via the power source 202 in similar fashion. This provides the user with a visible light while trying to use the pen or stylus in a dimly lit environment, for example. The LED may be also mounted at or near the touch tip 106w of the body 106b and may optionally be covered by the transparent lens cap.

The at least one ultraviolet radiation emitting device 106u can be a source of a UVA radiation, a UVB radiation, a UVC radiation, and a combination of UVA, UVB, and UVC radiations. The radiation type is chosen such that the radiation enables sterilization or destruction of the pathogens present on the stylus or a portion thereof. The intensity of the ultraviolet radiation emitting device 106u can be increased or decreased depending upon the pathogen type. Further, the time period for which the stylus 100 is irradiated with the ultraviolet radiation, which ensures that the pathogens are substantially killed or destructed.

UV light wavelengths for the application may range from 90 nm to 400 nm. Ultraviolet light, such as ultraviolet C (UVC; i.e., electromagnetic radiation or light having a wavelength from about 100 nm to about 280 nm, such as 254 nm), has been known to have a microbicide and bactericidal effects on air, liquids, and surfaces. In some embodiments, a wavelength set to 254 nm is effective at eliminating bacteria (e.g. *Naegleria fowleri*) in the following lifecycle stages: Cyst, trophozoite, and flagellate. In such embodiments, the ultraviolet (UV) dosage utilized for the inactivation of the *N. fowleri* in water is 63 mWsec/cm$^2$. Other electromagnetic radiation wavelengths may also be effective for disinfecting, sanitizing and/or sterilizing, including but not limited to wavelengths from about 270 nm to about 320 nm. In one embodiment, the UV light has a UV strength of at least 0.2, 0.25. 0.3, 0.4, 0.5 or more mW/cm$^2$. In another embodiment, the UV light has a UV strength of at least 1, 2, 5, 10, 25, 50 or more mW/cm$^2$.

The delivered energy is usually measured in millijoules per square centimeter (mJ/cm$^2$). It is desirable to deliver individual flashes that each have individual energy levels of less than about 10 mJ/cm$^2$, 5 mJ/cm$^2$, or 2 mJ/cm$^2$ and to deliver a sufficient number of flashes to provide a minimum total accumulated energy of 15 mJ/cm$^2$, or at least 30 mJ/cm$^2$, or at least 50 mJ/cm$^2$. The total accumulated energy depends on an operator's goal of using the flash lamp system, e.g., the types of contaminants an operator desires to deactivate or kill.

The at least one ultraviolet radiation emitting device 106u can be disposed anywhere on the body 106b, and the component radiating enclosure 104 or the at least one ultraviolet radiation emitting device 106u can be partly disposed on the body 106b, and the component radiating enclosure 104.

The self-sanitizing stylus 100 of the present disclosure is provided with the power source 202 which can be for example a battery. The power source or battery is lightweight and small in size. The battery can be for example a button cell type battery. Alternatively, the battery can be a dry cell battery. Yet another alternative can be lithium-ion battery. The battery or the power source employed herein can be any other type of power source or battery. For example, the battery can be use and throw type battery or a rechargeable battery.

The self-sanitizing stylus 100 may be powered by battery, as described above. In one embodiment, the battery can be chargeable such that the self-sanitizing stylus 100 can be plugged into a power source such as a USB wall plug outlet to recharge the battery.

In one embodiment, a sleeve or case may be provided to disinfect the self-sanitizing stylus 100. The case may be a hard-cover case with a hollow cavity sized to receive the self-sanitizing stylus 100. The interior of the case may be provided with a UV light, illuminating the interior of the case with disinfecting UV light to disinfect the outer surfaces of the self-sanitizing stylus 100. The case may have a battery and/or an electric circuitry that enables the case to be plugged in to a power source such as a wall outlet. This allows the user to set the self-sanitizing stylus 100 in the case while the case is plugged in, and leave the self-sanitizing stylus 100 in the case for an extended period of time without fear of the disinfecting ability of the case losing power.

The switch 204 is a switch selected from a toggle switch and a push button switch. Any other type of switch 204 can be used instead and the present disclosure is not limited by these specific examples listed herein above. The switch 204 can be disposed anywhere on the component retaining enclosure 104, or it can be disposed separated from the component retaining enclosure 104.

In accordance with one non-limiting embodiment, the self-sanitizing stylus further comprises at least one transducer 206 to deliver vibrational energy to the component retaining enclosure 104 to generate and deliver a haptic feedback upon pressing the switch 204. Thus, when a user presses the switch 204, a haptic feedback is generated by the at least one transducer 206 which provides the user holding the stylus 100 a signal that the ultraviolet radiation emitting device 106u would be emitting ultraviolet light, so that the user takes required precaution and avoids direct contact with the ultraviolet radiation emitted by the ultraviolet radiation emitting device 106u.

Alternatively, the feedback may be provided in form of an audio signal, a visual signal, and a haptic signal or any combinations thereof. The stylus 100 accordingly comprises at least one of an audio signal generator 208 and a visual signal generator 210. The audio signal generator 208 and the visual signal generator 210 are activated upon pressing the switch 204. Each of the audio signal generator 208 and the visual signal generator 210 are independently adapted to generate an audio signal and a visual signal, respectively.

A control system 212 may be provided, which is coupled to each of the switch 204, the power source 202, the at least one ultraviolet radiation emitting device 106u, the transducer 206, the audio signal generator 208, and the visual signal generator 210. The control system 212 may be provided to regulate the operation of the stylus in a manner described insofar in the present disclosure.

In accordance with the embodiments of the present disclosure, the touch screen device is one selected from the group consisting of a mobile phone, a laptop, and a desktop. The present disclosure is not limited to these and any other device which includes use of stylus or a similar type of device is also well within the ambit of the present disclosure.

In accordance with another aspect of the present disclosure, a method for self-sanitizing the stylus 100 which being used in combination with a touch screen device is disclosed.

The method for self-sanitizing the stylus 100 comprises writing in combination with the touch screen device by employing the self-sanitizing stylus 100 as described herein above. To activate the ultraviolet radiation emitting device 106u, the switch 204 is pressed to establish an electrical connection between the at least one ultraviolet radiation emitting device 106u and the power source 202. The at least one ultraviolet radiation emitting device 106u emits ultraviolet radiation which are incident on at least a portion of the body 106b of the longitudinal member 106, thereby disinfecting the portion of the body 106b being irradiated with the ultraviolet radiation.

The teachings are highly flexible in practice and are also highly scalable in that these teachings will accommodate any number (and type) of UV emitters and virtually any type, size, and shape of stylus. The installation and use of such a self-sanitizing stylus 100 system can also be a relatively simple process that requires little user training.

There are various approaches and methodologies known in the art to employ a series of captured images of a moving object such as a stylus in order to develop information that follows the movement of at least a portion of that object (such as the object's touch tip or writing tip). The present teachings are not particularly sensitive to the selection of any given such approach. So configured, a stylus can be readily provided and made available for convenient use with any touchpad at a time of need.

While the self-sanitizing stylus 100 shows a body member being a cylindrical shape, other embodiments are possible. For example, the geometric shape of the body member may be chosen such that it has at least one cross sectional area having a shape chosen from the group consisting of a circle, an oval, a triangle, rectangle, a pentagon, a hexagon, an octagon, and a diamond. A non-circular symmetric shape may prevent the self-sanitizing stylus 100 from inadvertently rolling off a sloped surface, for example a desk.

The grip portion of the body 106b may comprise any suitable material having the weight, stiffness, and other mechanical properties to enhance the user experience both aesthetically and functionally. A suitable material for the grip portion of the body member may include a metal such as brass, stainless steel, aluminum, and titanium. A suitable material may also include non-metals such as glass, gem, plastic, ceramic, graphite-reinforced composite materials, and wood-derived materials.

One of the considerations in designing the body 106b is improving the surface finish to minimize slipping in user's hand, especially in the presence of moisture. In this connection, in an embodiment of the present invention, the surface of the body member may include an anti-slip surface produced at least in part by sanding. In another embodiment, the surface may include an anodized surface. In these embodiments, the degree of sanding and anodization is chosen to achieve a degree of surface roughness in the grip portion of the body 106b suitable for gripping without slipping in user's hand.

The foregoing description of the specific embodiments have been described herein above that a person having ordinary skill in the art can apply the current knowledge, readily modify, or adapt for various applications such specific embodiments without departing from the generic concept. All such adaptations and modifications are intended to be comprehended within the meaning and range of equivalents of the disclosed embodiments.

Further, it is to be understood that the terminology employed herein is for the purpose of description and not of limitation. Therefore, while the embodiments herein have been described in terms of preferred embodiments, a person having ordinary skill in the art will readily recognize that the embodiments herein can be practiced with modification within the spirit and scope of the embodiments as described herein.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A self-sanitizing stylus for use in combination with a touch screen device, the self-sanitizing stylus comprising
 a body defined by
  a component retaining enclosure, and
  a longitudinal member extending from the component retaining enclosure;
  wherein the longitudinal member having a body defined between:
   a distal end with a touch tip operatively disposed thereon; and
   a proximal end secured with an operative end of the component retaining enclosure;
  wherein the body having at least one ultraviolet radiation emitting device disposed thereon;
  wherein the component retaining enclosure comprises:
   a power source; and
   a switch connected between the power source, and the at least one ultraviolet radiation emitting device, the switch adapted to selectively establish an electrical connection between the power source and the at least one ultraviolet radiation emitting device upon being switched ON, and power the at least one ultraviolet radiation emitting device, wherein the at least one ultraviolet radiation emitting device emits ultraviolet radiation, which is incident on at least a portion of the body of the longitudinal member thereby disinfecting the portion of the body; and
   at least one transducer to deliver vibrational energy to the component retaining enclosure to generate and deliver a haptic feedback upon pressing the switch.

2. The self-sanitizing stylus as claimed in claim 1, further comprising at least one of an audio signal generator, and a visual signal generator upon pressing the switch, wherein the audio signal generator and the visual signal generator each being independently adapted to generate an audio signal and a visual signal.

3. The self-sanitizing stylus as claimed in claim 1, further comprising
a control system coupled with and for managing each of the switch, the power source, and the at least one ultraviolet radiation emitting device, the transducer, the audio signal generator, and the visual signal generator.

4. A self-sanitizing stylus for use in combination with a touch screen device, the self-sanitizing stylus comprising:
a body defined by
a component retaining enclosure, and
a longitudinal member extending from the component retaining enclosure;
wherein the longitudinal member having a body defined between:
a distal end with a touch tip operatively disposed thereon; and
a proximal end secured with an operative end of the component retaining enclosure;
wherein the body having at least one ultraviolet radiation emitting device disposed thereon
wherein the component retaining enclosure including:
a power source; and
a switch connected between the power source, and the at least one ultraviolet radiation emitting device, the switch adapted to selectively establish an electrical connection between the power source and the at least one ultraviolet radiation emitting device upon being switched ON, and power the at least one ultraviolet radiation emitting device, wherein the at least one ultraviolet radiation emitting device emits ultraviolet radiation, which is incident on at least a portion of the body of the longitudinal member thereby disinfecting the portion of the body; and
wherein the touch screen device is one selected from the group consisting of a mobile phone, a laptop, and a desktop.

5. A method for self-sanitizing a stylus which being used in combination with a touch screen device, the method for self-sanitizing the stylus comprising writing in combination with the touch screen device by employing the self-sanitizing stylus, pressing the switch to establish an electrical connection between the at least one ultraviolet radiation emitting device and the power source, wherein the at least one ultraviolet radiation emitting device emits ultraviolet radiation which being incident on at least a portion of the body of the longitudinal member, thereby disinfecting the portion of the body being irradiated with the ultraviolet radiation; and wherein the device further comprises at least one transducer to deliver vibrational energy to the component retaining enclosure to generate and deliver a haptic feedback upon pressing the switch.

6. The method as claimed in claim 5, further comprising at least one of an audio signal generator, and a visual signal generator upon pressing the switch, wherein the audio signal generator and the visual signal generator each being independently adapted to generate an audio signal and a visual signal.

7. The method as claimed in claim 5, further comprising:
a control system coupled with and for managing each of the longitudinal member, switch, the power source, and the at least one ultraviolet radiation emitting device.

8. The method as claimed in claim 5, wherein the touch screen device is one selected from the group consisting of a mobile phone, a laptop, and a desktop.

* * * * *